United States Patent [19]

Nychka et al.

[11] 4,042,524

[45] Aug. 16, 1977

[54] METHODS FOR ABSORPTION HEATING

[75] Inventors: Henry R. Nychka, East Aurora; Richard E. Eibeck, Orchard Park; Chien C. Li, Williamsville, all of N.Y.

[73] Assignee: Allied Chemical Corporation, Morris Township, N.J.

[21] Appl. No.: 567,044

[22] Filed: Apr. 10, 1975

[51] Int. Cl.$^2$ ................................................ C09K 5/04
[52] U.S. Cl. ........................................ 252/69; 62/112; 126/247; 165/105; 252/67; 252/170; 252/171; 260/347.8
[58] Field of Search ................... 252/67, 69, 170, 171; 260/347.8; 126/247; 62/112; 165/105

[56] References Cited

U.S. PATENT DOCUMENTS

| 2,040,898 | 5/1936 | Zellhoefer | 252/69 |
|---|---|---|---|
| 2,040,905 | 5/1936 | Zellhoefer | 252/69 |
| 2,997,478 | 8/1961 | Walter et al. | 260/347.8 |
| 3,643,455 | 2/1972 | Hensel et al. | 62/112 |
| 3,668,134 | 6/1972 | Lambert et al. | 252/89 |

*Primary Examiner*—Mayer Weinblatt
*Attorney, Agent, or Firm*—Alan M. Doernberg; Anthony J. Stewart; Jay P. Friedenson

[57] ABSTRACT

The invention comprises a novel compound having the chemical name 2-(t-butoxymethyl) tetrahydrofuran and a novel absorption pair comprising 2-(t-butoxymethyl) tetrahydrofuran as the solvent and a lower alkyl fluorocarbon as the solute. The invention further comprises a method of absorption heating and method of absorption refrigeration using the novel absorption pair and absorption heating and an absorption cooling apparatus using the novel absorption pair.

1 Claim, No Drawings

METHODS FOR ABSORPTION HEATING

This invention relates to a method of absorption heating and refrigeration, a novel absorption pair for utilization in the method and an improved absorption heating and refrigeration apparatus.

In view of diminishing fossil fuel supplies, and hence, increasing fuel costs, there is a need to minimize the amount of fuel society consumes to heat habitable space.

The heat pump concept, wherein available energy taken from an ambient source such as outside air, and combined with fuel energy to heat space, is not new. Existing concepts include electrically driven-vapor compression heat pumps and absorption heat pumps. The latter require an absorber (or absorption) pair which comprises a solvent and a solute wherein the solvent remains a liquid, which may be a solution, throughout the operation of the apparatus, and the solute having a liquid and vapor phase in the cycles of the operation. The solute must be soluble in the solvent and must be readily separable as a vapor from the solvent by means of evaporation. In addition, the solute must be suitable for condensation from the vapor back to a liquid form. In general, all absorption heating and refrigeration apparatus require essentially the same parts and function in essentially the same way regardless of the particular solute and solvent used. The major components of the apparatus are a generator, condenser, evaporator, absorber and absorption pair. The solute passes through all units and the solvent, sometimes also known as the absorbent, is confined to movement through the generator and absorber.

In operation, a mixture of absorbent and solute is heated in the generator to boil off most or all of the solute which rises as a vapor through a connecting conduit to the condenser. The mixture may be heated in the generator by any suitable means such as a gas flame, geothermal heat, solar heat or warm water.

The generator and condenser operate at relatively high pressure, so the condensing temperature of the solute is sufficiently high to permit rejecting the latent heat emitted by the condensing solute to outside air or cooling water passing through or around the condenser.

The liquid solute leaving the condenser passes through a conduit to a throttling valve, through the throttling valve and through another conduit to the evaporator. The throttling valve throttles the liquid solute to a lower pressure so it will boil at a relatively low temperature in the evaporator and thus absorb heat from air or water passing through or around the evaporator.

The vaporized solute passes from the evaporator through a conduit to the absorber where is is dissolved in cool absorbent which has been carried to the absorber by means of a conduit connecting the absorber with a generator outlet. The mixture of absorbent and solute resulting in the absorber then passes through a conduit to the generator where it is reheated to continue the process.

Any suitable material of construction for the apparatus may be used which can withstand the encountered temperature, pressure and corrosive properties, if any, of the solvent and solute. Such a heat absorption apparatus is particularly desirable since moving parts, if any, are minimal when compared with the moving parts found in electrically driven-vapor compression heat pumps.

Unfortunately, the known solute/solvent systems for heat pumps have serious disadvantages. The most common solute/solvent pair (absorber pair) is ammonia/water. The ammonia/water pair has a disadvantage since the heating and cooling efficiency of apparatus utilizing the ammonia/water absorber pair is not as high as desired; i.e. the coefficient of performance (COP)h practically attainable is less than about 1.50 and at low generator temperature, i.e., below 180° F., and at high generator temperature, i.e., above 220° F., is below about 1.3 and the (COP)c practically obtainable is generally less than about 0.4 and at high or low generator temperatures becomes even lower. (COP)h is a measure of the efficiency of the absorption cycle when used for heating and is the ratio of the heat output to the energy input. (COP)c is a measure of the efficiency of the absorption cycle when used for cooling and is the ratio of heat removed to the energy input. The ammonia/water combination has additional disadvantages. Water is highly volatile, thus preventing complete separation of the ammonia from the water in the generator at high generator temperatures. The condensing pressure required to condense the ammonia is undesirably high, thus requiring equipment capable of withstanding such pressure.

The only other commercial absorber pair is lithium bromide/water wherein water is used as the solute and lithium bromide is used as the absorbent. The water/lithium bromide absorber pair has undesirable characteristics. For example, water as a solute is limited to an evaporation temperature of above about 32° F., which is its freezing point. Lithium bromide is not sufficiently soluble in water to permit the absorber to be air cooled. The extremely low pressures in in the system require large vapor conduits. Unless the system is precisely controlled, lithium bromide can crystallize and cause fouling of the system and the generator temperature cannot efficiently operate below 185° F. nor above 215° F. Additionally, aqueous lithium bromide solutions are corrosive, this requiring special alloys for suitable apparatus.

Other absorber pairs which have been suggested have not been commercially accepted due to one or more disadvantages. Such disadvantages include difficulty and expense in manufacturing one or both members of the pair, a lack of sufficient affinity of the absorbent for the solute vapor, thus preventing sufficient absorption of the solvent vapor to draw in and compress the solute. The absorber pairs have frequently not been mutually soluble over the whole range of operating conditions, thus permitting crystallization and the formation of solid particles which make it difficult or impossible for proper fluid circulation. The absorbent has frequently been volatile, thus preventing the refrigerant vapor leaving the generator from being pure. When absorbent evaporates from the generator, the efficiency of the system is frequently substantially reduced since energy input is wasted in evaporation. Additionally, the absorbent pairs previously suggested are frequently toxic or are highly flammable. Absorption pairs suggested in the prior art frequently have unacceptably high or unacceptably low working pressures. The working pressures should be as near to atmospheric pressure as possible to minimize equipment weight and minimize leaking into or out of the system. In addition, pressure difference between the high side and low side is frequently too high to facilitate circulation of the solution. The solutes suggested in the prior art frequently have a latent heat of evaporation which is unacceptably low, thus requiring large quantities of fluids to be circulated and the coefficient of performance of other absorber pairs suggested in the prior art is usually too low for serious consideration in commercial apparatus.

BRIEF DESCRIPTION OF THE INVENTION

In accordance with this invention, there is provided a novel absorber pair for absorption heating and refrigeration which has a high coefficient of performance, has a relatively high flash point, operates at approximately atmospheric pressure and has low toxicity. In addition, both pair members can be readily and inexpensively manufactured. The high coefficient of performance is due to a strong affinity between the solute and solvent, good mutual solubility over the whole range of operating conditions, good absorbent volatility and a solute having a high latent heat of vaporization. The solvent in the absorber pair is a novel compound, namely, 2-(t-butoxymethyl) tetrahydrofuran, of the formula

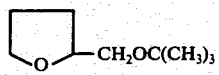

The novel absorption pair comprises from about 4 to about 60 percent of a fluorocarbon solute selected from dichloromonofluoromethane, monochlorodifluoromethane, trifluoromethane and monochloromonofluoromethane dissolved in the 2-(t-butoxymethyl) tetrahydrofuran compound by weight of said compound.

The novel methods of the invention comprise using the previously described absorption pair in known prior art absorption heating and refrigeration methods.

The novel improved absorption heating or refrigeration apparatus of the invention comprise known prior art absorption heating or refrigeration apparatus components in conjunction with one of the foregoing lower alkyl fluorocarbon solutes in 2-(t-butoxymethyl) tetrahydrofuran as the absorption pair.

DETAILED DESCRIPTION OF THE INVENTION

The novel 2-(t-butoxymethyl) tetrahydrofuran solvent composition is readily and inexpensively prepared in high yield from tetrahydrofurfuryl alcohol, isobutylene and a catlytic amount of sulfuric acid.

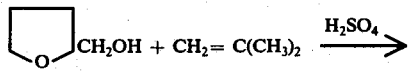

The preferred fluorocarbon for use in the preferred absorption pair due to both high (COP)$h$ and (COP)$c$ is dichloromonofluoromethane. The quantity of fluorocarbon to be used in conjunction with 2-(t-butoxymethyl) tetrahydrofuran solvent is from about 4 to about 60 percent fluorocarbon by weight of solvent. The preferred quantity of fluorocarbon is from about 10 to about 40 percent by weight of solvent.

The methods of absorption heating or refrigeration comprise absorbing gaseous lower alkyl fluorocarbon solute in 2-(t-butoxymethyl) tetrahydrofuran solvent to release heat of solution in the vicinity of an area to be heated, or in the case of use in refrigeration, away from the area to be cooled; heating the resulting solution in the vicinity of an area of be heated, or in the case of use in refrigeration, away from the area to be cooled, to release gaseous fluorocarbon from the solvent; condensing the released fluorocarbon to form liquid fluorocarbon in the vicinity of an area to be heated, or in the case of refrigeration away from an area to be cooled; evaporating the liquid fluorocarbon at a location removed from the vicinity of the area to be heated, or in the case of refrigeration in the vicinity of an area to be cooled; and returning the evaporated fluorocarbon for reabsorption into the solvent.

EXAMPLE 1

Preparation of 2-(t-butoxymethyl) tetrahydrofuran.

153 grams of tetrahydrofurfuryl alcohol (THFA) and 9.8 grams of sulfuric acid are added to a 250 ml flask provided with a dry ice packed condenser, a thermometer and agitator. 32 grams of isobutylene are bubbled through the THFA over a period of 50 minutes at 60° to 65° C. The reaction mixture is then allowed to reflux for one hour. The resulting mixture is then analyzed by gas chromatography and is found to contain a 70% theoretical yield of 2-(t-butoxymethyl) tetrahydrofuran, the balance of the mixture being unreacted tetrahydrofurfuryl alcohol and sulfurcic acid with a small percentage of unreacted isobutylene.

EXAMPLE 2

40 weight percent dichloromonofluoromethane solute in 2-(t-butoxymethyl) tetrahydrofuran solvent by weight of solvent, is introduced into an absorption heating apparatus consisting essentially of a generator, condenser, evaporator, and absorber. The condenser is cooled with water to maintain a temperature of 125° F. in the condenser and absorber, and a gas flame is provided under the generator to obtain a generator temperature of 300° F. A throttling valve is provided between the condenser and evaporator which is adjusted to maintain an evaporator temperature of 45° F. and a high pressure in the generator and condenser and a lower pressure in the evaporator and absorber. The heat or energy input provided by the gas flame is calculated by determining the volume of gas burned. The heat output is determined by measuring the temperature rise in a known volume of water which is recycled around the condenser and absorber. The (COP)$h$ for the absorption system is calculated to be 1.540 and the (COP)$c$ is calculated to be 0.527, both of which indicate high efficiency.

EXAMPLE 3

Example 2 is repeated except the generator temperature is decreased to 250° f. The (COP)$h$ is calculated to be 1.460 and the (COP)$c$ is calculated to be 0.454, both of which indicate a high efficiency at such a low generator temperature.

EXAMPLE 4

Example 2 is repeated except the generator temperature is decreased to 200° F. The (COP)$h$ is calculated to be 1.350 and the (COP)$c$ is calculated to be 0.345, both of which indicate a high efficiency at such a low generator temperature.

We claim:

1. In a heating method wherein a gaseous solute is dissolved in a solvent to release heat of solution in the vicinity of an area to be heated, the resulting solution is heated to release gaseous solute from the solvent, the released solute is condensed to form liquid solute and to release heat of condensation in the vicinity of the area to be heated and evaporating the resulting liquid solute at a location removed from the area to be heated, the improvement comprising using a fluorocarbon selected from the group consisting of dichloromonofluoromethane, monochlorodifluoromethane, trifluoromethane and monochloromonofluoromethane as the solute and 2-(t-butoxymethyl) tetrahydrofuran as the solvent.

* * * * *